US009277859B2

(12) United States Patent
Oyaizu et al.

(10) Patent No.: US 9,277,859 B2
(45) Date of Patent: Mar. 8, 2016

(54) OPTICAL TOMOGRAPHIC IMAGING APPARATUS AND METHOD FOR CONTROLLING THE SAME

(71) Applicant: CANON KABUSHIKI KAISHA, Tokyo (JP)

(72) Inventors: Keisuke Oyaizu, Kawasaki (JP); Hiroshi Aoki, Saitama (JP); Yukio Sakagawa, Tokyo (JP); Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 14/164,049

(22) Filed: Jan. 24, 2014

(65) Prior Publication Data

US 2014/0211158 A1   Jul. 31, 2014

(30) Foreign Application Priority Data

Jan. 31, 2013   (JP) .................................. 2013-017658

(51) Int. Cl.
*A61B 3/10*   (2006.01)
(52) U.S. Cl.
CPC ....................................... *A61B 3/102* (2013.01)
(58) Field of Classification Search
CPC ...... A61B 3/14; A61B 3/102; G01B 9/02091; G01B 9/02063; G01B 9/02064; G01B 9/02089

USPC .................. 351/206, 221, 246, 205; 356/479
See application file for complete search history.

(56) References Cited

U.S. PATENT DOCUMENTS

2008/0151256 A1* 6/2008 Kikawa et al. ................ 356/496
2011/0170062 A1* 7/2011 Isogai et al. .................. 351/206

FOREIGN PATENT DOCUMENTS

| CN | 102727174 A | 10/2012 |
| CN | 103222850 A | 7/2013 |
| JP | 2009-160190 A | 7/2009 |
| JP | 2011147612 A | 8/2011 |

* cited by examiner

*Primary Examiner* — Bumsuk Won
*Assistant Examiner* — Wen Huang
(74) *Attorney, Agent, or Firm* — Canon USA Inc. IP Division

(57) ABSTRACT

An optical tomographic imaging apparatus includes an instruction unit configured to issue an instruction on a size of an imaging range of a tomographic image, and a control unit configured to control a measurement light optical path length changing unit to perform alignment in a depth direction with respect an object after the instruction by the instruction unit, and change an optical path length of measurement light by a distance corresponding to a change of the size on which the instruction is issued.

18 Claims, 12 Drawing Sheets

OPTICAL TOMOGRAPHIC IMAGING APPARATUS AND METHOD FOR CONTROLLING THE SAME

BACKGROUND OF THE INVENTION

1. Field of the Invention

The present invention relates to an optical tomographic imaging apparatus and a method for controlling the same. For example, the present invention relates to an optical tomographic imaging apparatus for use in ophthalmic practice and a method for controlling the same.

2. Description of the Related Art

Optical image measurement techniques for forming an image of the surface and/or inside of an object to be measured by using light are attracting attention in recent years. Unlike conventional X-ray computed tomography (CT), the optical image measurement techniques are not invasive to the human body. Applications of the optical image measurement techniques are expected to be developed especially in the medical field. Significant progress has been made in the ophthalmological field in particular.

Among typical techniques for optical image measurement is a method called optical coherence tomography (OCT). This method uses an interferometer, which enables high-resolution high-sensitivity measurement. Using wideband weak light as illumination light provides an advantage of high safety to a subject.

An optical tomographic imaging apparatus based on OCT (hereinafter, referred to as an OCT apparatus) using optical interference can obtain a tomographic image of a sample with high resolution. In particular, the OCT apparatus relates to an anterior eye optical tomographic imaging apparatus for forming an image of an anterior eye of a subject's eye.

The OCT apparatus can irradiate a sample with low coherent light serving as measurement light, and measure backscattered light from the sample with high sensitivity by using an interference system or an interference optical system. The OCT apparatus can scan the sample with the measurement light to obtain a high-resolution tomographic image. A tomographic image of a cornea region of the anterior eye of a subject's eye can thus be obtained and used for ophthalmic diagnosis.

Japanese Patent Application Laid-Open No. 2011-147612 discusses an optical tomographic imaging apparatus that can capture both a tomographic image of an anterior eye and a tomographic image of a fundus. According to whether an imaging mode is an anterior eye imaging mode or a fundus imaging mode, the optical tomographic imaging apparatus moves a reference mirror included in its interference optical system to a position corresponding to the imaging mode.

SUMMARY OF THE INVENTION

According to an aspect of the present invention, an optical tomographic imaging apparatus configured to obtain a tomographic image of an object based on light into which return light from the object irradiated with measurement light and reference light corresponding to the measurement light are combined includes a measurement light optical path length changing unit configured to change an optical path length of the measurement light, an instruction unit configured to issue an instruction on a size of an imaging range of the tomographic image, and a control unit configured to control the measurement light optical path length changing unit to perform alignment in a depth direction with respect to the object after the instruction by the instruction unit, and change the optical path length of the measurement light by a distance corresponding to a change of the size on which the instruction is issued.

Further features of the present invention will become apparent from the following description of exemplary embodiments with reference to the attached drawings.

DESCRIPTION OF THE EMBODIMENTS

Take the case of changing the size of the imaging range of a tomographic image of an object such as a subject's eye. A possible method may include changing the optical path length of measurement light by moving the apparatus main body with respect to the object in an optical axis direction. with such a method, an operator cannot readily know how much the optical path length of the measurement light is to be changed to obtain a tomographic image of the size intended by the operator.

In view of the foregoing issue, an aspect of an exemplary embodiment is directed to providing an optical tomographic imaging apparatus and a method for controlling the same, by which the operator can easily obtain a tomographic image of the intended size by designating the size of the imaging range of the tomographic image of an object.

According to the present exemplary embodiment, if an instruction on the size of the imaging range of the tomographic image is issued, the optical path length of the measurement light can be changed according to the instruction. The operator can thus obtain a tomographic image of the intended size by designating the size of the imaging range of the tomographic image of an object.

An optical tomographic imaging apparatus (OCT apparatus) according to a first exemplary embodiment will be described below.

[General Configuration of Apparatus]

A general configuration of the optical tomographic imaging apparatus according to the present exemplary embodiment will be described with reference to FIG. 1.

Figure 1:
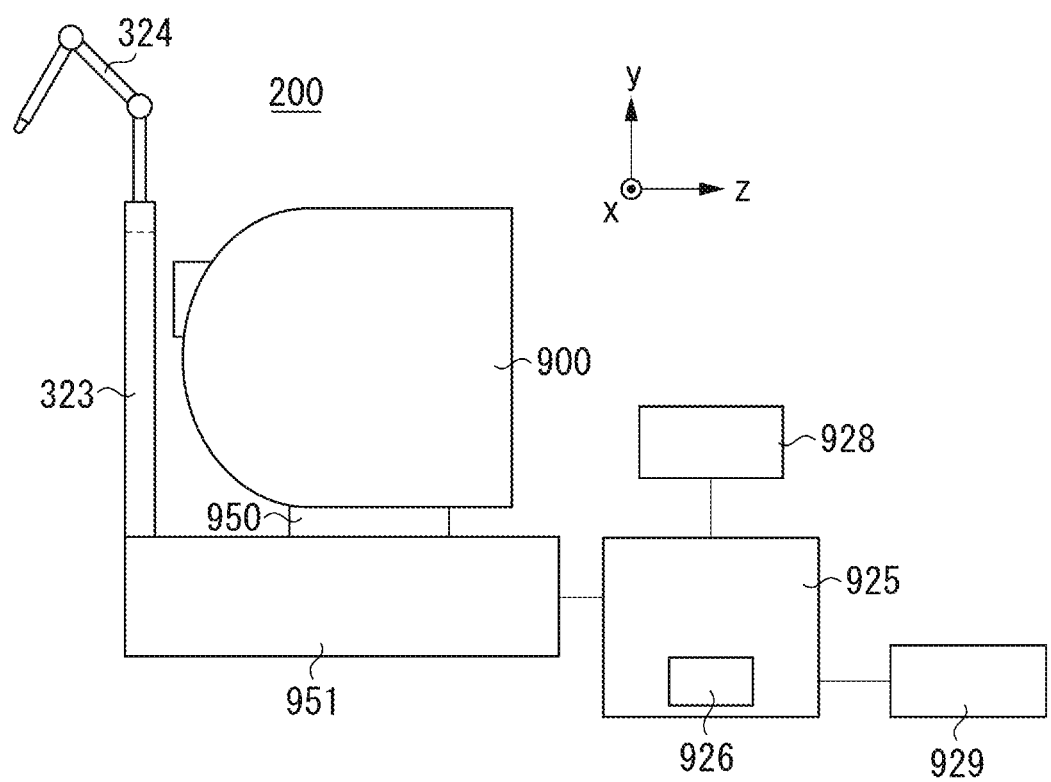
FIG. 1 is a diagram illustrating an entire optical tomographic imaging apparatus according to a first exemplary embodiment.

FIG. 1 is a side view of the optical tomographic imaging apparatus. The optical tomographic imaging apparatus 200 includes an optical head 900 which includes a measurement optical system for capturing a two-dimensional image and a tomographic image of an anterior eye. A stage unit 950 is a moving unit that can move the optical head 900 in x, y, and z directions in the diagram by using not-illustrated motors. A base unit 951 includes a spectroscope to be described below. The optical head 900, an example of an optical unit including an optical path of measurement light, is a housing of the measurement optical system. The stage unit 950 is an example of an optical unit moving mechanism that moves with respect to an object.

A personal computer 925 constructs a tomographic image. The personal computer 925 also serves as a control unit of the stage unit 950 and controls the stage unit 950. A hard disk 926 stores a program for tomographic imaging. The hard disk 926 also serves as a subject information storage unit. A monitor 928 serves as a display unit. An input unit 929 is used to issue instructions to the personal computer 925. Specifically, the input unit 929 includes a keyboard and a mouse. A chin support 323 fixes the chin and forehead of a subject to prompt the subject to fix the eyes (subject's eyes). An external fixation lamp 324 is used to fix the subject's eyes. The external fixation lamp 324 and an internal fixation lamp to be described below can be switched and used.

[Configuration of Measurement Optical System and Spectroscope]

A configuration of the measurement optical system and the spectrometer according to the present exemplary embodiment will be described with reference to FIG. 2.

The interior of the optical head 900 will be described. Objective lenses 101-1 and 101-2 are located opposite a subject's eye 100. A reflecting mirror 102 and a dichroic mirror 103 are arranged on an optical axis of the objective lenses 101-1 and 101-2. By the reflecting mirror 102 and the dichroic mirror 103, light from the object lenses 101-1 and 101-2 is branched into optical paths L1 and L2 of respective different wavelength bands. The optical path L1 is an optical path of an OCT optical system. The optical path L2 is intended for anterior eye observation and for an internal fixation lamp.

The optical path L2 is further branched by a third dichroic mirror 104 into optical paths to a charge-coupled device (CCD) 105 for anterior eye observation and an internal fixation lamp 106 according to respective wavelength bands like described above. Lenses 101-3, 107, and 108 are arranged on the optical path L2. A not-illustrated motor drives the lens 107 for the purpose of a focusing adjustment intended for the internal fixation lamp 106 and anterior eye observation. The CCD 105 has sensitivity to wavelengths of not-illustrated anterior eye observation illumination light. Specifically, the CCD 105 has sensitivity to wavelengths around 780 nm. The internal fixation lamp 106 generates visible light and prompts eye fixation of the subject.

The optical path L1 constitutes the OCT optical system as described above. The optical path L1 is intended to capture a tomographic image of an anterior eye 100-1 of the subject's eye 100. More specifically, the optical path L1 is intended to obtain an interference signal for forming a tomographic image. A lens 101-4, a mirror 113, an X scanner 114-1, a Y scanner 114-2, and lenses 115 (OCT focus lens 115) and 116 are arranged on the optical path L1. The X scanner 114-1 and the Y scanner 114-2 are intended to scan the anterior eye 100-1 of the subject's eye 100 with light. Light from a light source 118 is emitted from a fiber 117-2 connected to a photocoupler 117. A not-illustrated motor drives the lens 115 to focus and adjust the light emitted from the fiber 117-2 on the anterior eye 100-1. By such a focusing adjustment, light from the anterior eye 100-1 is also incident on and forms a spot-like image on the end of the fiber 117-2. The lens 115, also referred to as an OCT focus lens, is an example of a focusing lens.

A configuration of optical paths from the light source 118, a reference optical system, and the spectroscope will be described.

The light source 118, a reference mirror 119, dispersion compensation glass 120, the photocoupler 117 described above, single mode optical fibers 117-1 to 117-4 integrally connected with the photocoupler 117, an lens 121, and the spectroscope 180 constitute a Michelson interferometer.

The light emitted from the light source 118 passes through the optical fiber 117-1 and is split into measurement light on the side of the optical fiber 117-2 and reference light on the side of the optical fiber 117-3 through the photocoupler 117. The measurement light passes through the optical path of the OCT optical system described above. The fundus of the subject's eye 100 to be observed is irradiated with the measurement light. The measurement light is reflected and scattered by the retina, and passes through the same optical path to reach the photocoupler 117.

The reference light passes through the optical fiber 117-3, the lens 121, and the dispersion compensation glass 120 to reach the reference mirror 119. The dispersion compensation glass 120 is inserted to adjust dispersion of the reference light to that of the measurement light. The reference light is reflected by the reference mirror 119 and returns through the same optical path to reach the photocoupler 117. The photocoupler 117 combines the measurement light and the reference light into interference light. Interference occurs when an optical path length of the measurement light and that of the reference light satisfy a predetermined condition. The reference mirror 119 is supported to be adjustable in the optical axis direction by a not-illustrated motor and a not-illustrated drive mechanism. The optical path length of the measurement light varies depending on the anterior eye 100-1. The reference mirror 119 can adjust the optical path length of the reference light to that of the measurement light. The interference light is guided through the optical fiber 117-4 to the spectroscope 180.

The spectroscope 180 includes lenses 181 and 183, a diffraction grating 182, and a line sensor 184. The interference light emitted from the optical fiber 117-4 is converted into generally parallel light through the lens 181. The generally parallel light is spectrally dispersed by the diffraction grating 182, and focused on the line sensor 184 by the lens 183. The line sensor 184 is an example of a light receiving element that receives the interference light and generates and outputs an output signal according to the interference light in the present exemplary embodiment.

Next, the light source 118 will be described. The light source 118 is a super luminescent diode (SLD), which is a typical low coherent light source. The light source 118 has a center wavelength of 855 nm and a wavelength bandwidth of approximately 100 nm. The bandwidth is an important parameter since the bandwidth influences resolution of the resulting tomographic image in the optical axis direction. While an SLD is selected as the light source 118, any type of light source that can emit low coherent light may be used. Examples include an amplified spontaneous emission (ASE) device. In view of eye measurement, near infrared light has a suitable center wavelength. Since the center wavelength influences the resolution of the resulting tomographic image in a lateral direction, the center wavelength can be as short as possible. From both reasons, the center wavelength of 855 nm is employed.

In the present exemplary embodiment, a Michelson interferometer is used as the interferometer. A Mach-Zehnder interferometer may be used instead. Which interferometer to use may be determined according to a difference in light intensity between the measurement light and the reference light. If the difference in light intensity is large, a Mach-Zehnder interferometer can be used. If the difference in light intensity is relatively small, a Michelson interferometer can be used.

[Method for Obtaining Tomographic Image]

A method for obtaining a tomographic image by using the optical tomographic imaging apparatus will be described. The optical tomographic imaging apparatus can obtain a tomographic image of a desired region of the anterior eye 100-1 of the subject's eye 100 by controlling the X scanner 114-1 and the Y scanner 114-2.

Figure 3:
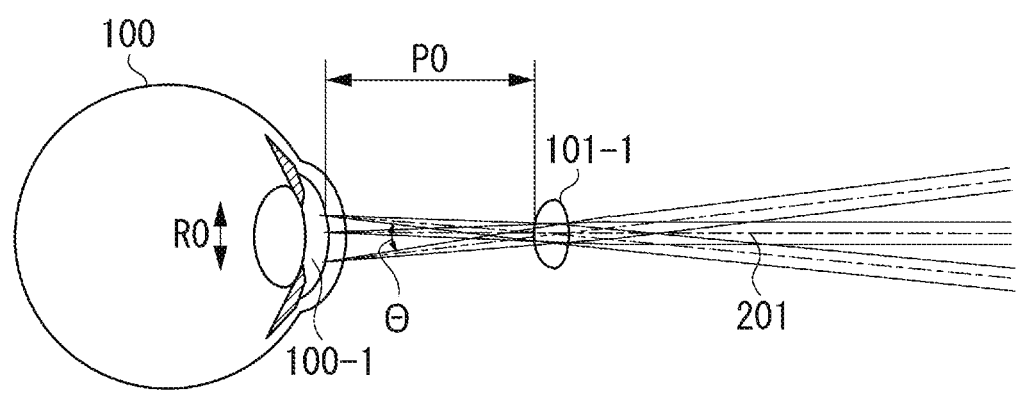
FIG. 3 is an explanatory diagram illustrating a state where an anterior eye of a subject's eye is scanned in an x direction according to the first exemplary embodiment.
Figure 3:
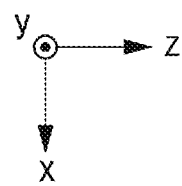

FIG. 3 illustrates a state where the subject's eye 100 is irradiated with measurement light 201 and the anterior eye 100-1 is scanned in the x direction. The line sensor 184 captures information about a predetermined number of images from an imaging range of the anterior eye 100-1 in the x direction. A fast Fourier transform (FFT) is performed on a luminance distribution on the line sensor 184 obtained in a position in the x direction. A linear luminance distribution obtained by the FFT is converted into density or color information for monitor display. Such density or color information will be referred to as an A scan image. According to the output signal obtained from the interference light received by the line sensor 184 serving as the light receiving element, the optical tomographic imaging apparatus obtains A scan images. The plurality of A scan images is arranged into a two-dimensional image, which will be referred to as a B scan image. After the plurality of A scan images for constructing a B scan image is obtained, the optical tomographic imaging apparatus moves the scan position in the y direction and performs a scan in the x direction again. In such a manner, the optical tomographic imaging apparatus obtains a plurality of B scan images. The plurality of B scan images or a three-dimensional tomographic image constructed from the plurality of B scan images is displayed on the monitor 928. The operator can use the displayed image(s) to diagnose the subject's eye 100.

The angle of view or the imaging range for obtaining a tomographic image of the anterior eye 100-1 is usually determined according to a scan range R0 in the x direction illustrated in FIG. 4A to be described below. The scan range R0 is determined by a scan angle θ of the X scanner 114-1 and an imaging distance P0 from the objective lens 101-1 to the anterior eye 100-1 of the subject's eye 100. In other words, to change the size of the imaging range, the scan angle θ or the imaging distance P0 can be changed. The imaging distance P0 can be easily changed by changing the optical path length of the measurement light, such as by moving the optical head 900 in the z-axis direction. In the present exemplary embodiment, the imaging distance P0 is changed by changing the optical path length of the measurement light of the optical head 900. Such a configuration will be defined as a measurement light optical path length changing unit. There are other configurations for changing the optical path length of the measurement light than that of the present exemplary embodiment. The measurement light optical path length changing unit according to the present exemplary embodiment is defined as a concept covering such configurations.

To obtain a desired interference by combining the measurement light and the reference light, the optical path length of the measurement light and the optical path length of the reference light need to be interlocked to satisfy a predetermined condition as described above. According to the optical path length of the measurement light in the position of the anterior eye 100-1 where the imaging distance is P0, the reference mirror 119 is thus moved to change the optical path length of the reference light.

The reference mirror 119 and a configuration for moving the reference mirror 119 are an example of a reference light optical path length changing unit for changing the optical path length of the reference light according to the present exemplary embodiment. As described above, to obtain interference by the combined light, the optical path length of the reference light needs to be changed according to the optical path length of the measurement light. For example, in the present exemplary embodiment, the personal computer 925 includes a module area that functions as a control unit (also referred to as an "optical path length interlocking unit"). The control unit causes the reference light optical path length changing unit to change the optical path length of the reference light in an interlocking manner with the change of the optical path length of the measurement light by the measurement light optical path length changing unit.

Figure 4A:
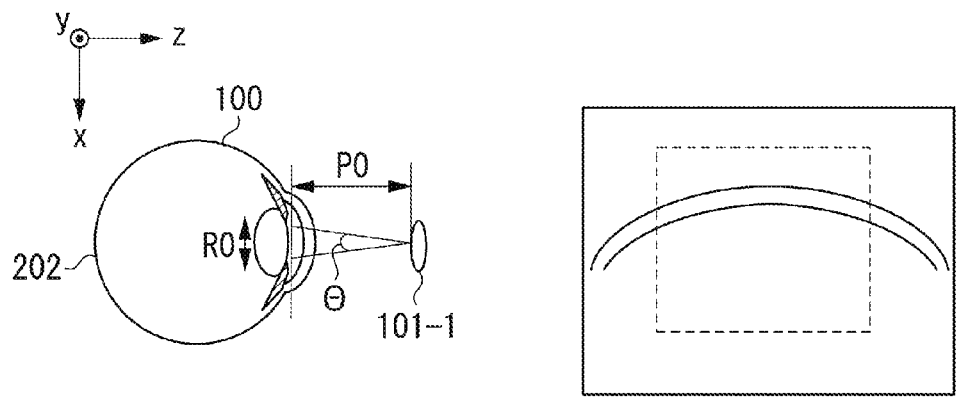
FIGS. 4A, 4B, and 4C are explanatory diagrams illustrating scan ranges in an imaging position of an anterior eye according to the first exemplary embodiment and images obtained according to the scan ranges.
Figure 4B:
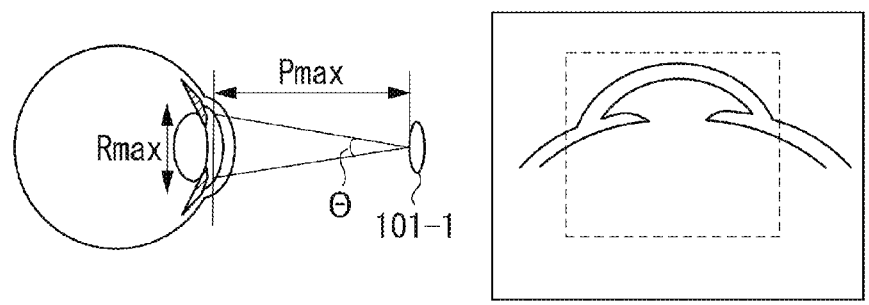
Figure 4C:
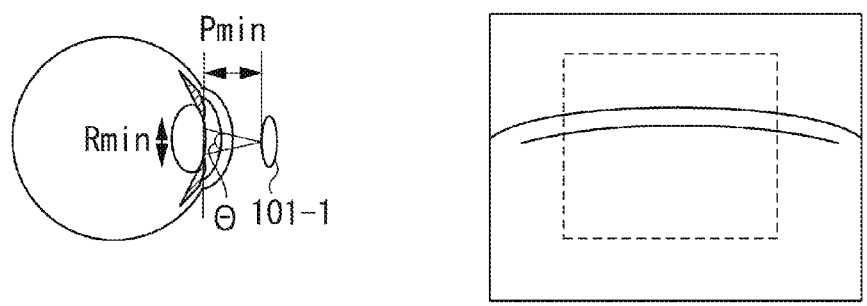

FIGS. 4A, 4B, and 4C illustrate diagrams illustrating the scan ranges in the position of the anterior eye 100-1 when the imaging distance P0 is changed, and corresponding tomographic images displayed in the respective angles of view. By changing the imaging distance P0 and moving the reference mirror 119 according to the change, the optical tomographic imaging apparatus can change the size of the imaging range of the anterior eye 100-1 without changing the scan angle θ. FIG. 4B illustrates a case where the imaging distance P0 is changed to Pmax to increase the distance between the subject's eye 100 and the optical tomographic imaging apparatus, and the reference mirror 119 is moved to a position equivalent to the imaging distance Pmax. In such a case, the anterior eye 100-1 can be imaged with a wide scan range (angle of view) Rmax. FIG. 4C illustrates a case where the imaging distance P0 is changed to Pmin to reduce the distance between the subject's eye 100 and the optical tomographic imaging apparatus, and the reference mirror 119 is moved to a position equivalent to the imaging distance Pmin. In such a case, the anterior eye 100-1 can be imaged with a magnifying scan range Rmin.

[Measurement Operation Screen]

Figure 5:
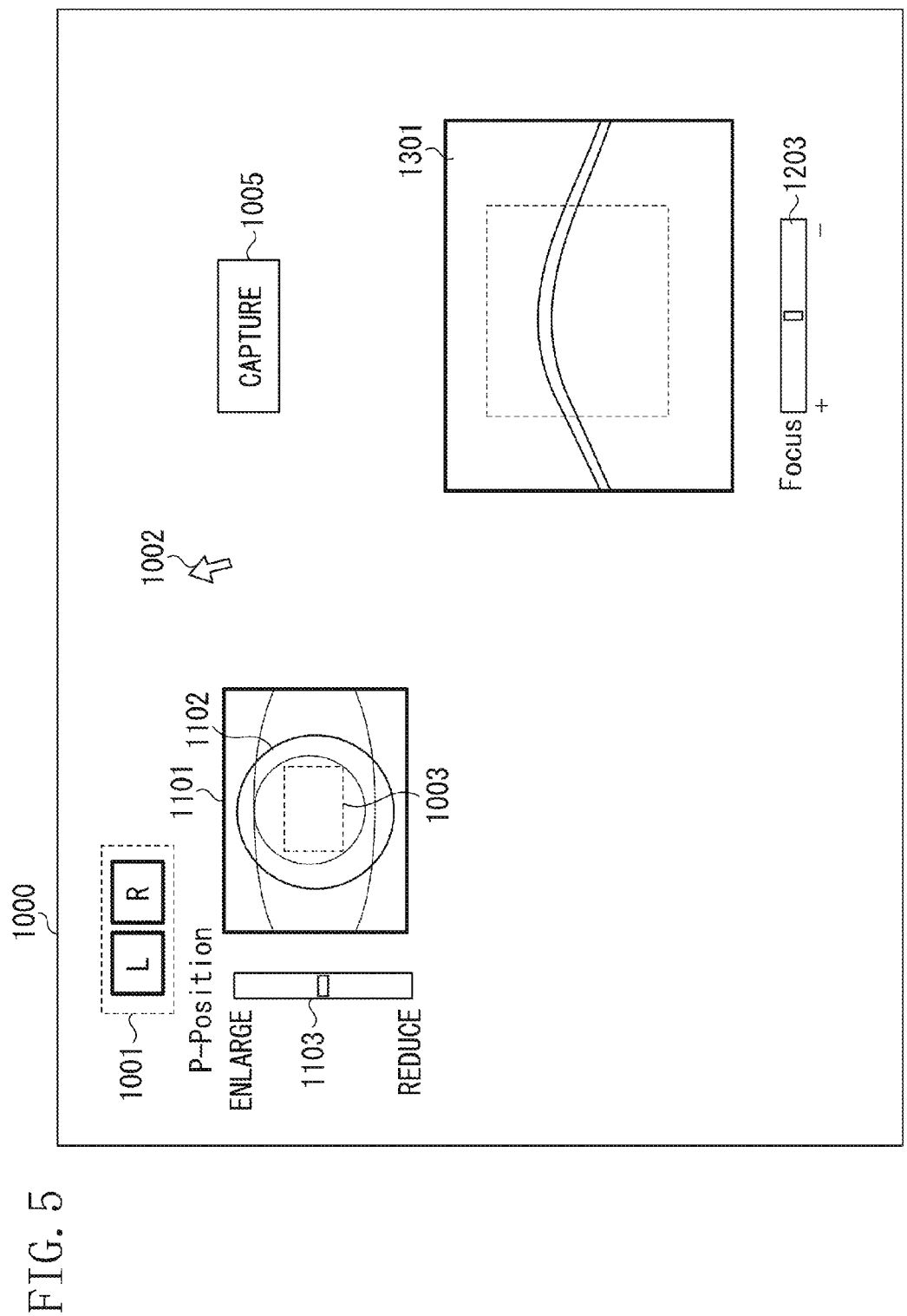
FIG. 5 is a diagram illustrating an example of a measurement operation screen according to the first exemplary embodiment.
Figure 6:
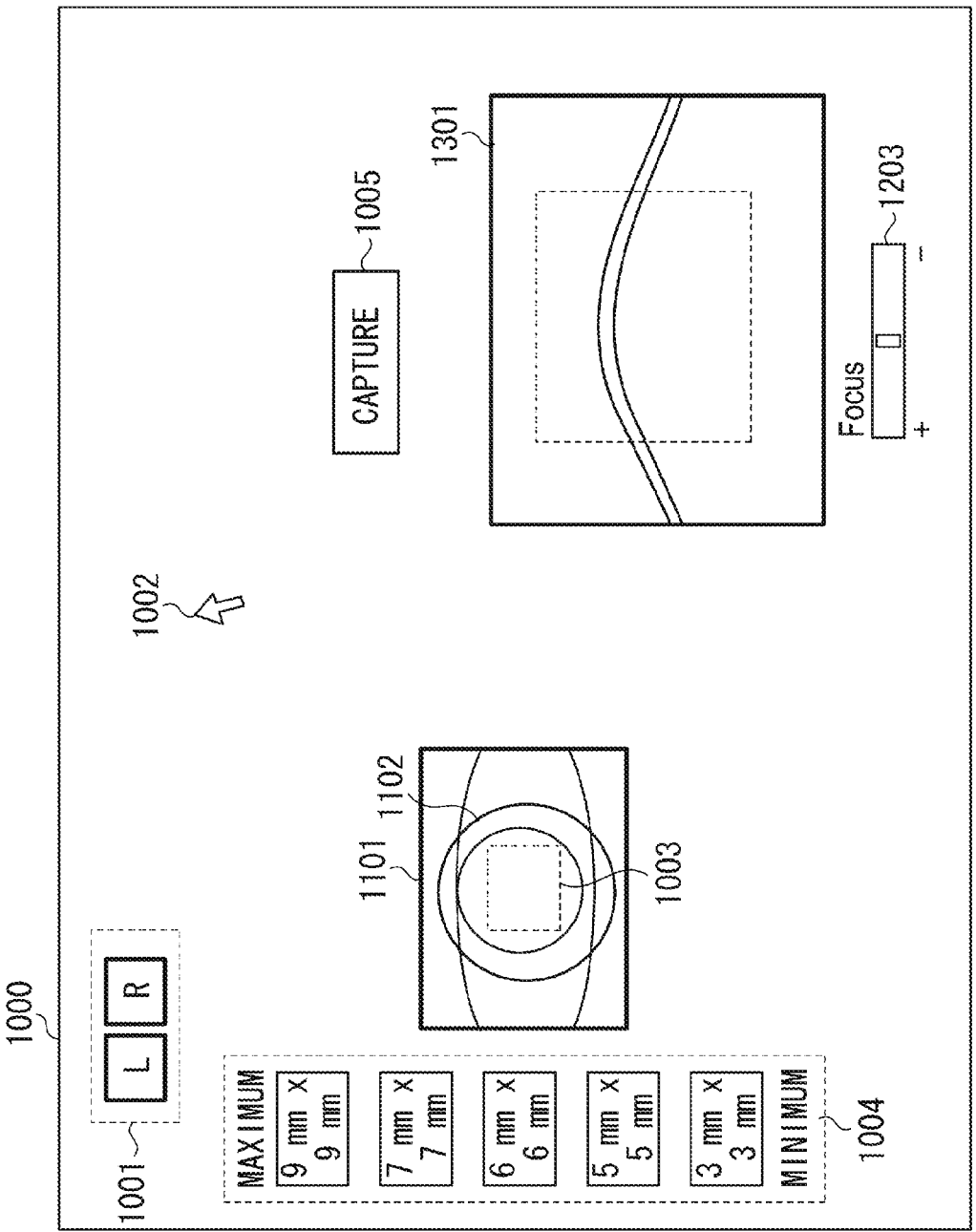
FIG. 6 is a diagram illustrating another example of the measurement operation screen according to the first exemplary embodiment.

Next, a measurement operation screen according to the present exemplary embodiment will be described with reference to FIGS. 5 and 6. FIG. 5 is a diagram illustrating an example of a measurement operation screen 1000 according to the present exemplary embodiment. FIG. 6 is a diagram illustrating another example of the measurement operation screen 1000 according to the present exemplary embodiment.

An anterior eye observation screen 1101 displays an anterior eye image 1102 obtained by the CCD 105 for anterior eye observation. A tomographic image display screen 1301 is intended to check a tomographic image obtained. L and R buttons 1001 are intended to switch between subject's left and right eyes. The L and R buttons 1001 are pressed to move the optical head 900 to initial positions for the left and right eyes, respectively. When the operator operates the mouse included in the input unit 929, a position of a mouse cursor 1002 moves. This optical tomographic imaging apparatus is configured so that a mouse cursor position detection unit can change an alignment unit according to the position of the mouse cursor 1002. The mouse cursor position detection unit calculates the position of the mouse cursor 1002 from a pixel position of the mouse cursor 1002 on-screen. Ranges are set on the measurement operation screen, and correspondence between the set ranges and alignment drives is set in advance. If the mouse cursor 1002 falls within the pixels of a set range, alignment defined for the set range can be performed. Alignment operations by the mouse are performed by rotating a wheel of the mouse.

Sliders 1103 and 1203 arranged near the respective images are intended for adjustment. The slider 1103 is intended to specify the imaging distance P0 to the subject's eye 100. When the slider 1103 is moved, a character 1003 in the anterior eye observation screen 1101 changes in size in an interlocking manner. The size of the character 1003 is also interlocked with a change in the size of the imaging range (angle of view) of the anterior eye 100-1, whereby the lens 107 for anterior eye observation is moved to a predetermined position. The lens 107 is an example of an anterior eye observation unit including a focus lens that performs focusing on the anterior eye 100-1 according to the present exemplary embodiment. An upper limit of the slider 1103 corresponds to the imaging range Rmax of the anterior eye 100-1 described above. A lower limit of the slider 1103 corresponds to the imaging range Rmin of the anterior eye 100-1. The slider 1203 is intended to perform an OCT focus adjustment. The OCT focus adjustment is an adjustment for moving the lens 115 in the direction indicated by an arrow illustrated in FIG. 2 to make a focusing adjustment with respect to the anterior eye 100-1. The sliders 1103 and 1203 are also configured to move in an interlocking manner with alignment operations performed in the respective images by using the mouse. More specifically, the control unit (also referred to as a "focus interlocking unit") of the personal computer 925 causes the OCT focus lens 115 to perform focusing on the anterior eye 100-1 in an interlocking manner with the change of the optical path length of the measurement light by the measurement light optical path length changing unit, either independent of or in an interlocking manner with the OCT focus adjustment by the slider 1203. The focusing operation of the anterior eye observation unit on the anterior eye 100-1 needs to be performed according to a change in the optical path length of the measurement light, which is accompanied by a change in the imaging distance P0. In the present exemplary embodiment, the foregoing control unit (also referred to as an "anterior eye focusing interlocking unit") causes the anterior eye observation unit to perform focusing on the anterior eye 100-1 in an interlocking manner with the change of the optical path length of the measurement light by the measurement light optical path length changing unit.

FIG. 6 illustrates the measurement operation screen 1000 in which the slider 1103 illustrated in FIG. 5 is replaced with imaging range selection buttons 1004. Settings include a standard (R0=6 mm×6 mm), a maximum (Rmax=9 mm×9 mm), and a minimum (Rmin=3 mm×3 mm). If the operator selects any one of the imaging range selection buttons 1004, the optical tomographic imaging apparatus can change the size of the imaging range of a tomographic image accordingly. The optical tomographic imaging apparatus can change the size of the imaging range even if the operator makes such a selection without an anterior eye image 1102 obtained.

[Flow for Obtaining Tomographic Image of Anterior Eye]

Figure 7:
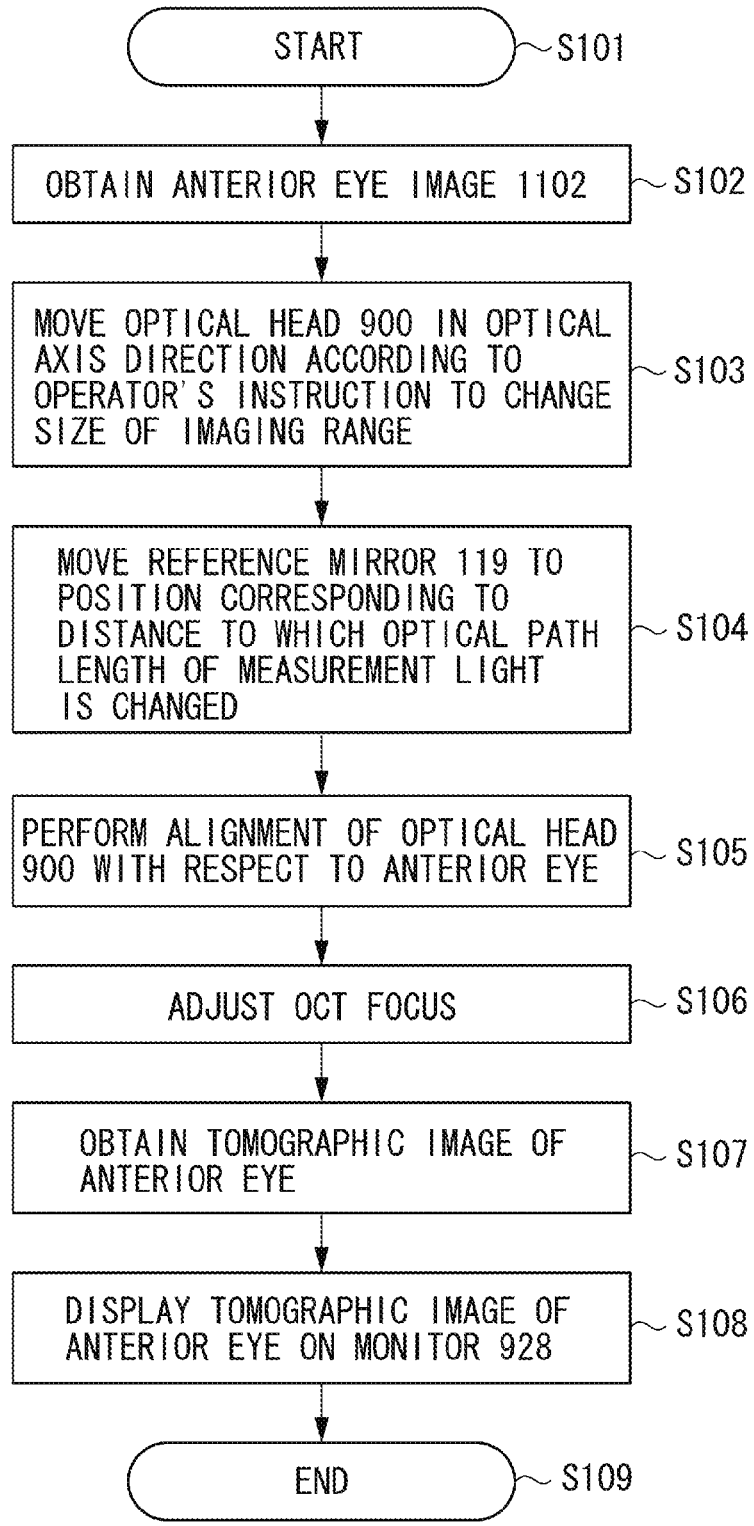
FIG. 7 is a flowchart illustrating a measurement flow according to the first exemplary embodiment.

A flow for obtaining a tomographic image of an anterior eye 100-1 by using the OCT apparatus according to the present exemplary embodiment will be described with reference to FIG. 7. FIG. 7 is a flowchart illustrating a measurement flow according to the present exemplary embodiment. The flowchart illustrates operations of the operator and the personal computer 925.

In step S101, the personal computer 925 starts the present measurement flow. In step S102, the optical tomographic imaging apparatus obtains an anterior eye image 1102 according to an instruction from the personal computer 925. The subject's eye 100 is illuminated with not-illustrated anterior eye illumination light. Reflected light passes through the object lenses 101-1 and 101-2 and the optical path L2 described above, and forms an image on the CCD 105. The anterior eye image 1102 formed on the CCD 105 is read by a not-illustrated CCD control unit, amplified, subjected to analog-to-digital (A/D) conversion, and input to a calculation unit. The anterior eye image 1102 input to the calculation unit is taken into the personal computer 925.

In step S103, the operator issues an instruction to the slider 1103 to change the size of the imaging range to a desired size by using the input unit 929, which issues instructions to the personal computer 925. A bar of the slider 1103 moves on-screen. According to the operator's instruction, the personal computer 925 serving as an example of the control unit moves the optical head 900 in the optical axis direction to a distance corresponding to the changed size. In step S104, the personal computer 925 serving as an example of the control unit performs control to move the reference mirror 119, according to the movement of the optical head 900, to a position corresponding to the distance to which the optical path length of the measurement light is changed. As a result, a coherence gate is adjusted so that an anterior eye tomographic image is located within an imaging frame. The personal computer 925 may move the lens 107 along with the movement of the reference mirror 119. When the personal computer 925 moves the optical head 900 and the reference mirror 119 in an interlocking manner according to the instruction to change the size of the imaging range, the personal computer 925 may also move the OCT focus lens 115 in an interlocking manner to change the focusing position. Instead of moving the reference mirror 119 in an interlocking manner, the personal computer 925 may move the OCT focus lens 115 in an interlocking manner. In such a case, step S106 to be described below may be omitted. The personal computer 925 may simultaneously move such members. The personal computer 925 may move such members with a time difference.

In step S105, the personal computer 925 serving as an example of the control unit moves the optical head 900 with respect to the anterior eye 100-1 according to instructions from the operator, thereby performing alignment of the optical head 900 with respect to the anterior eye 100-1. The alignment may be performed by moving the subject's face support with respect to the optical head 900. Aside from the operator's manual operations, the optical head 900 may move automatically. Specifically, the personal computer 925 detects a pupil position of the subject's eye 100 by image processing from the anterior eye image 1102 captured by the CCD 105. Based on the detected pupil position, the personal computer 925 can find out an alignment position relationship between the optical tomographic imaging apparatus and the subject's eye 100. The personal computer 925 can drive the optical head 900 by using a not-illustrated XYZ stage so that the detected pupil position of the subject's eye 100 comes to an ideal position. The personal computer 925 may keep track of the anterior eye 100-1 while capturing a tomographic image. In such a case, the operator can continue monitoring the anterior eye 100-1 of the subject's eye 100 with improved convenience.

In step S106, the operator issues an instruction to the slider 1203 to change the focusing position of the anterior eye tomographic image by using the input unit 929. A bar of the slider 1203 moves on-screen. According to the operator's instruction, the personal computer 925 serving as an example of the control unit performs control to move the OCT focus lens 115. In such a manner, an OCT focus can be adjusted. In step S107, the operator presses a capture button 1005 by using the input unit 929. According to the operator's instruction, the personal computer 925 serving as an example of the control unit performs control to obtain a tomographic image of the anterior eye 100-1. In step S108, the personal computer 925, serving as an example of a display control unit, causes the monitor 928 to display the tomographic image of the anterior eye 100-1. In step S108, the personal computer 925 may correct the tomographic image of the anterior eye 100-1 and cause the monitor 928 to display the corrected tomographic image. In step S109, the personal computer 925 ends the present measurement flow.

Note that the tomographic image obtained in step S107 may include a wider or narrower range of regions than, for example, a tomographic image obtained at the standard imaging distance P0 does in the screen of the same size. As will be described below, the correction is an operation for enlarging or reducing a display range (angle of view) so that the regions included in such captured images are displayed in the same size as that of the region obtained at the imaging distance P0. The above operation is performed by a module area of the personal computer 925, the module area functioning as an image correction unit for correcting and changing a display mode of an image. A module area functioning as the display control unit, which is included in the control unit, displays a cursor or a display pattern for issuing an instruction to change the imaging range on the display unit.

Figure 8A:
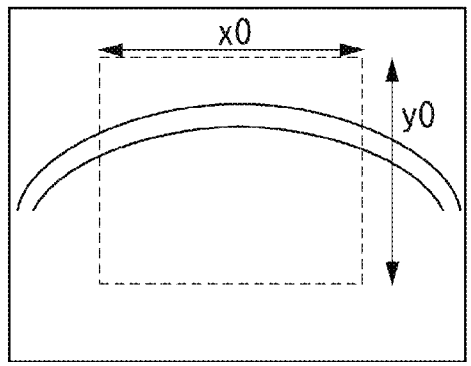
FIGS. 8A, 8B, 8C, 8D, 8E, and 8F are diagrams illustrating display examples of tomographic images of an anterior eye according to the first exemplary embodiment and display examples of the images corrected.
Figure 8B:
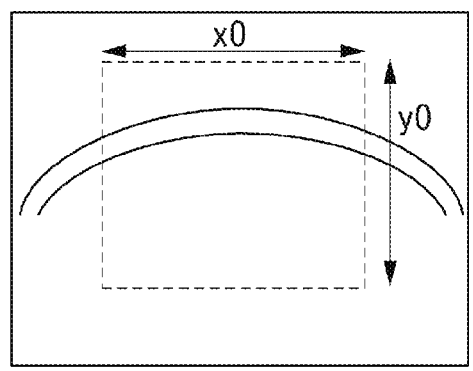
Figure 8C:
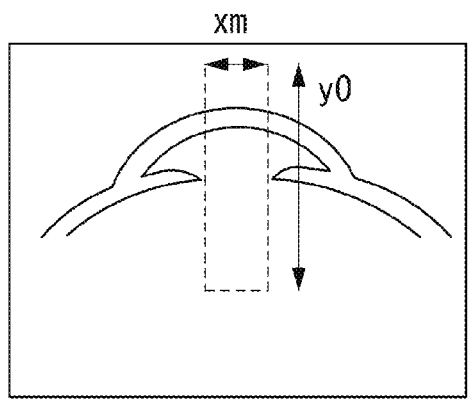
Figure 8D:
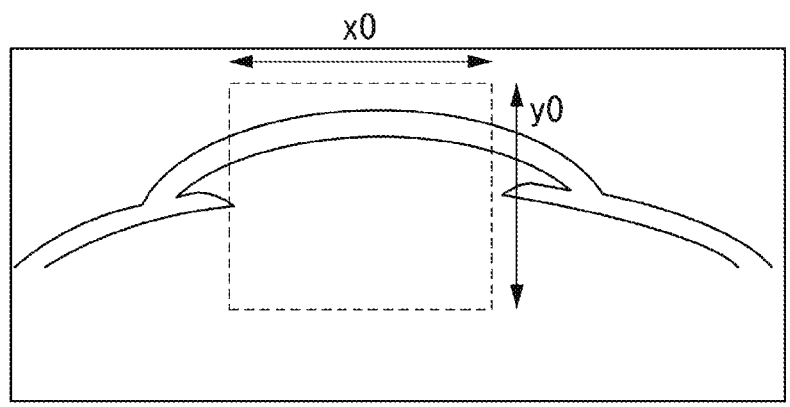
Figure 8E:
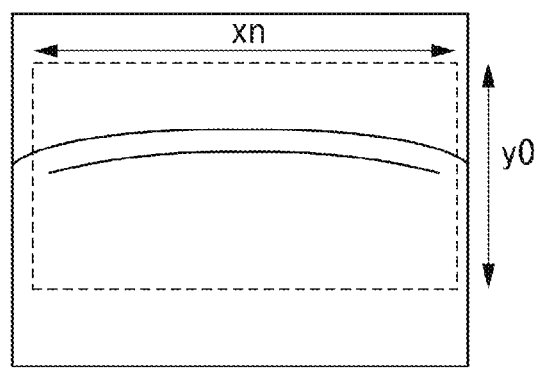
Figure 8F:
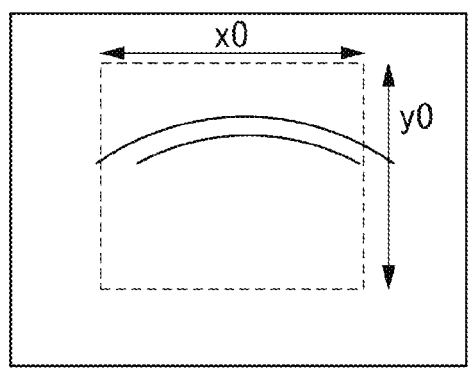

If the imaging distance P0 is greater than the standard imaging distance, the tomographic image of the anterior eye 100-1 becomes narrower only in the lateral direction without a change in tomographic depth. If the imaging distance P0 is smaller than the standard imaging distance, the tomographic image becomes wider only in the lateral direction without a change in the tomographic depth. FIGS. 8A, 8B, 8C, 8D, 8E, and 8F illustrate examples where display images of tomographic images of an anterior eye 100-1 are corrected. FIG. 8A illustrates a tomographic image of the anterior eye 100-1 with a lateral field of view x0 corresponding to the imaging distance P0. If the imaging distance P0 increases to Pmax, the lateral field of view x0 decreases to xm as illustrated in FIG. 8C. As illustrated in FIG. 8D, the lateral field of view xm can be easily converted into the field of view x0 and displayed by using a known image processing method. A tomographic image corresponding to the imaging distance Pmin can be similarly processed and displayed as illustrated in FIG. 8F. Various measurements may be performed based on the tomographic images illustrated in FIGS. 8D and 8F. Various measurements may be performed by using the original images illustrated in FIGS. 8C and 8E, multiplied by the respective ratios of the imaging distances P and the lateral fields of view X.

As described above, the optical tomographic imaging apparatus according to the present exemplary embodiment can provide an apparatus with which the operator can specify various imaging ranges and capture images. In other words, an optical tomographic imaging apparatus having various fields of view and high resolution can be provided while maintaining the performance of the optical systems. Since the operating distance between the subject's eye 100 and the optical tomographic imaging apparatus can be changed, burdens on the subject can be relieved by capturing an image with an increased operating distance according to the subject's condition.

[Designating Size of Imaging Range of Tomographic Image Before Alignment]

A second exemplary embodiment will be described with reference to FIG. 9. In the present exemplary embodiment, after the operator designates the size of the imaging range of a tomographic image, the personal computer 925 performs alignment (or realignment). The personal computer 925 then changes the optical path length of the measurement light by a distance corresponding to the designated size. As a result, the operator can reliably obtain a tomographic image of the intended size even if the alignment is disordered before the operator designates the size of the imaging range of the tomographic image.

Figure 2:
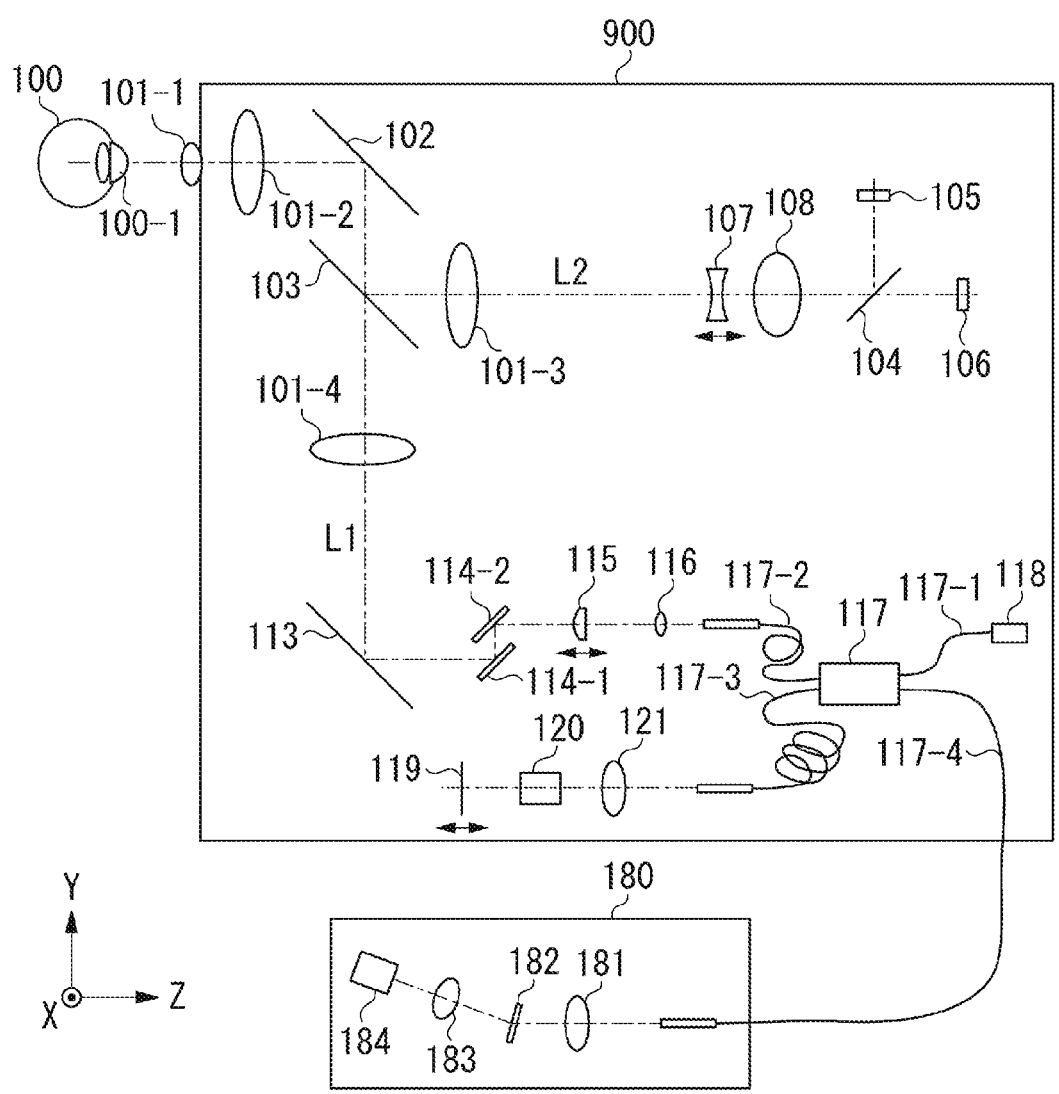
FIG. 2 is a diagram illustrating a configuration of a measurement optical system according to the first exemplary embodiment.
Figure 9:
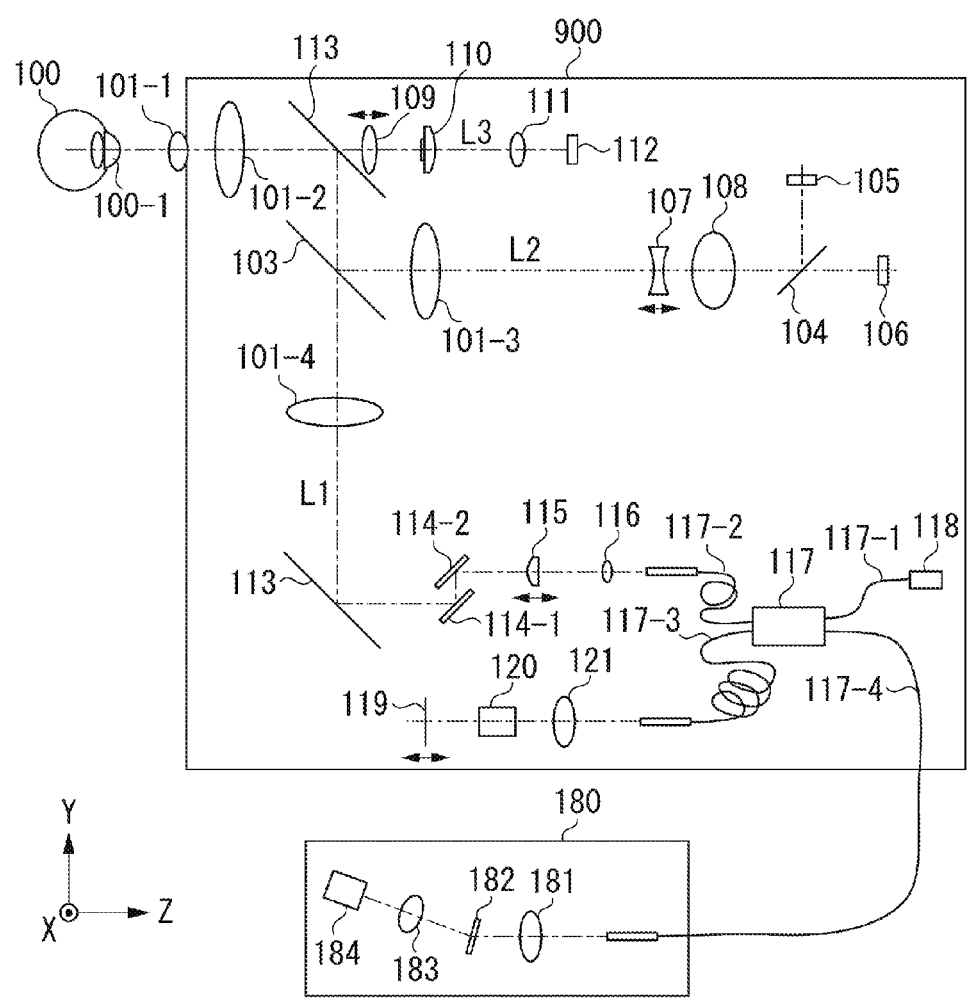
FIG. 9 is a diagram illustrating an entire optical tomographic imaging apparatus according to a second exemplary embodiment.

In the second exemplary embodiment, as illustrated in FIG. 9, the reflecting mirror 102 illustrated in FIG. 2 is replaced with a dichroic mirror 113, and there is provided an optical path L3 of an alignment optical system. A lens 109, a split prism 110, a lens 111, and a CCD 112 are arranged on the optical path L3. The CCD 112 is used to observe an anterior eye image. The split prism 110 is configured so that if the alignment in the Z direction (alignment in a depth direction with respect to the object) is not correct, a part of the anterior eye image deviates in position. If the alignment in the Z direction is correct, the positional deviation of a part of the anterior eye image disappears. The personal computer 925 can thus detect a misalignment in the Z direction based on the direction and amount of deviation of the anterior eye image. The personal computer 925 can move the apparatus main body with respect to the subject's eye 100 to eliminate such a misalignment in the Z direction, whereby the alignment in the Z direction can be performed. In the X and Y directions, the personal computer 925 can perform alignment by detecting a pupil position in an anterior eye observation image obtained by the CCD 112.

For example, to image a cornea thickness distribution, the operator specifies a wide imaging range so that the entire cornea can be imaged. For example, to image an iridocorneal angle, the operator specifies an image range as narrow as the iridocorneal angle can be imaged. A not-illustrated imaging mode selection unit may be configured to select an imaging mode such as an imaging region before obtaining a tomographic image. Before the operator designates the size of the imaging range of a tomographic image after the alignment, the personal computer 925 may perform alignment again so that the optical path length of the measurement light is reliably changed by the distance corresponding to the designated size. In such a case, the operator can designate the size of the imaging range while observing the anterior eye observation image.

[Adjusting Scan Angle if Change of Optical Path Length of Measurement Light Reaches its Limit]

Differences between an optical tomographic imaging apparatus (OCT apparatus) according to a third exemplary embodiment and the OCT apparatus described in the first exemplary embodiment will be described.

As illustrated in FIGS. 4B and 4C, the OCT apparatus described in the first exemplary embodiment can change the size of the imaging range of the anterior eye 100-1 without changing the scan angle θ of the scanning unit from FIG. 4A. In other words, the OCT apparatus can perform enlargement and reduction without changing the optical paths inside the optical head 900. This eliminates the need to consider the effect of aberrations at lens edges, the effect of shading of the light beam, and a change in a sampling density due to a change in the scan angle θ.

In the present exemplary embodiment, if the imaging distance P0 reaches the maximum imaging distance Pmax or the minimum imaging distance Pmin, the personal computer 925 can further change the scan angle θ to further change the imaging range. If the maximum imaging distance Pmax is reached, the personal computer 925 increases scanning amplitudes of the X scanner 114-1 and the Y scanner 114-2. As a result, the scan angle θ increases. This can further increase the scan range R0 to provide a reduced view of a wider range.

If the imaging range P0 reaches the minimum imaging distance Pmin and a further enlargement is desired, the personal computer 925 reduces the scanning amplitudes of the X scanner 114-1 and the Y scanner 114-2. This enables an enlarged view of a narrower scan range R0, whereby a further enlarged image can be obtained.

The maximum imaging distance Pmax is determined based on driving limits of the OCT focus lens 115 and the reference mirror 119. The imaging distance P0 can be increased to increase the scan range R0. As a result, a wider range can be viewed. In other words, a reduced image can be viewed. The minimum imaging distance Pmin is determined based on the foregoing driving limits of the OCT focus lens 115 and the reference mirror 119, as well as a distance at which the safety of the subject's eye 100 is secured from a viewpoint of contact between the subject's eye 100 and the OCT apparatus.

[Polygonal Mirror]

Figure 10A:
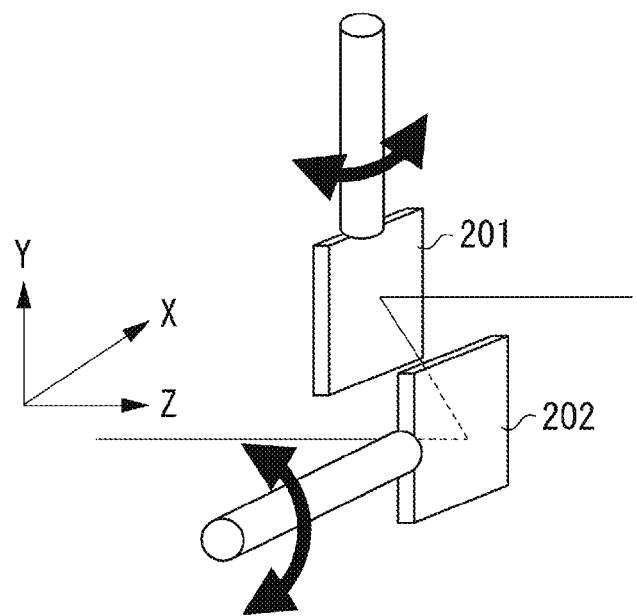
FIGS. 10A and 10B are diagrams illustrating a polygonal mirror according to a fourth exemplary embodiment.

A fourth exemplary embodiment will be described with reference to FIGS. 10A and 10B. In the first exemplary embodiment, the X scanner 114-1 and the Y scanner 114-2 are moved to obtain a tomographic image of a desired region. For example, as illustrated in FIG. 10A, the X scanner 114-1 and the Y scanner 114-2 may include mirrors 201 and 202, respectively, which make reciprocating rotational movements. The X scanner 114-1 and the Y scanner 114-2 may be configured so that a light beam incident on the mirrors 201 and 202 is swung to reciprocate in the X and Y directions. Examples of the mirrors 201 and 202 include galvanometer mirrors, which are driven by galvanometer motors having high positioning accuracy and repetitive reproducibility.

Figure 10B:
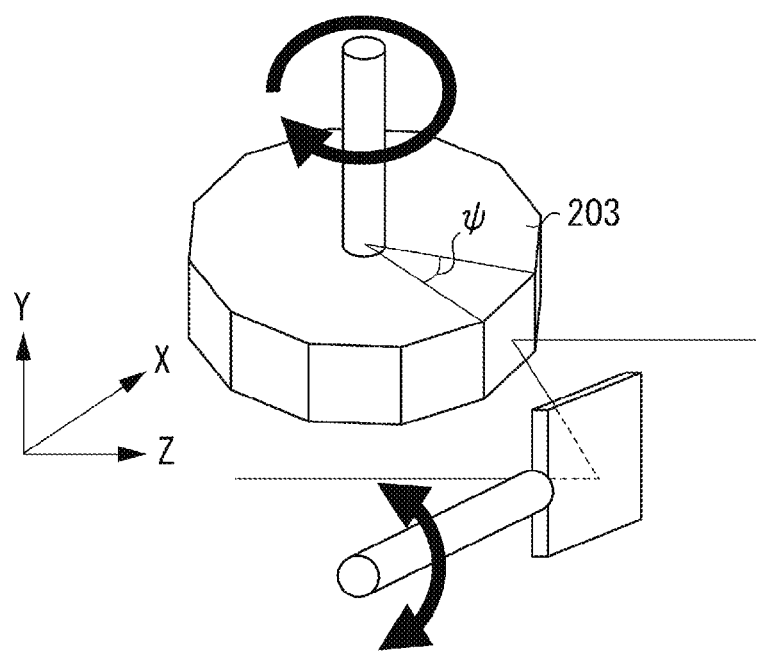

In the present exemplary embodiment, at least either one of the X scanner 114-1 and the Y scanner 114-2 is a polygonal mirror 203 rotatable in one direction such as illustrated in FIG. 10B. The angle of rotation ψ at which each surface of the polyhedron passes the incident position of the light beam determines the scanning width. New surfaces appear in the incident position of the light beam in succession, whereby the light beam can be repeatedly swung in the X or Y direction. Since the polygonal mirror moves in one direction, the polygonal mirror can perform scanning at higher speed than the foregoing galvanometer mirrors, which reciprocate the mirror surfaces.

If the foregoing galvanometer mirrors are used to reciprocate the mirror surfaces, the tilt angles of the galvanometer mirrors can be changed to change the scan widths. If a polygonal mirror is used, the scan width is uniquely determined by the shape of the polygonal mirror. The use of the polygonal mirror makes it difficult to change the size of the imaging range by changing the scan width. In such a case, the mechanism for changing the size of the imaging range described in the first exemplary embodiment can be used to change the size of the imaging range while increasing the scanning speed.

[Correspondence Table of Parameters]

A fifth exemplary embodiment will be described with reference to FIG. 11. If an instruction on the size of the imaging range of a tomographic image is issued, the personal computer 925 controls the optical path length of the measurement light, the optical path length of the reference light, OCT focusing, and anterior eye focusing in an interlocking manner. Correspondences between such parameters may be stored in the hard disk 926, serving as an example of a storage unit. The personal computer 925 can perform the foregoing control by referring to the stored correspondences.

Figure 11:
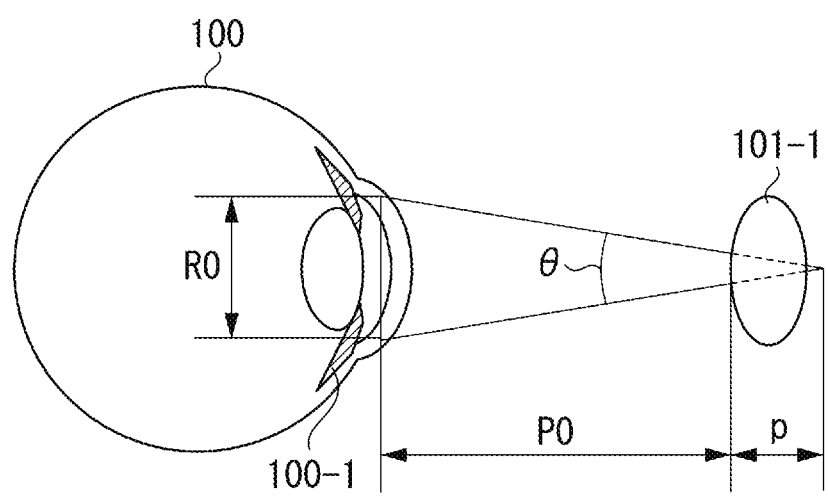
FIG. 11 is a diagram illustrating parameters according to a fifth exemplary embodiment.

For example, as illustrated in FIG. 11, correspondences between a scan width R0 which determines the imaging range, an optical path length P0 of the measurement light, an optical path length Pr of the reference light, an OCT focus lens position Lo, and an anterior eye focus lens position La may be determined by simulation in advance. A correspondence table thereof may be generated and stored in the hard disk 926. Based on the correspondence table, a relationship between the parameters may be determined as the following approximate expressions (1) to (4). Such expressions may be stored in the hard disk 926.

$$P0 = \frac{R0}{2\tan\left(\frac{\theta}{2}\right)} - p, \quad (1)$$

$$Pr = P0, \quad (2)$$

$$Lo = f_1(P0), \quad (3)$$

and $$La = f_2(P0), \quad (4)$$

where p is a distance between an intersection of extensions of scan area boundary lines spreading at an angle of θ from the objective lens 101-1 and a front vertex of the objective lens 101-1. p is a value determined by optical design, and can thus be determined by simulation in advance. The functions $f_1(P0)$ and $f_2(P0)$ are determined by the design of the optical systems. The functions $f_1(P0)$ and $f_2(P0)$ are approximate expressions of a relationship of the optical path length P0 of the measurement light to an OCT focus lens position Lo and an anterior eye focus lens position La at which appropriate OCT focusing and appropriate anterior eye focusing are obtained at the optical path length P0 of the measurement light. Such a relationship is determined by simulation in advance.

[Adjusting Size of Fixation Lamp According to Designated Size of Imaging Range]

Differences between an optical tomographic imaging apparatus (OCT apparatus) according to a sixth exemplary embodiment and the OCT apparatus described in the first exemplary embodiment will be described. The OCT apparatus described in the first exemplary embodiment changes the imaging distance P0 according to the scan range R0, thereby changing the optical path length of the measurement light. In such a case, the size of the fixation lamp 106 to the subject's eye 100 changes as well. The greater the imaging distance P0, the smaller the fixation lamp 106 appears. The smaller the imaging distance P0, the larger the fixation lamp 106 appears. As a result, the fixation lamp 106 can sometimes give the subject an unpleasant feeling, and sometimes become less visible.

The OCT apparatus according to the present exemplary embodiment is configured so that a not-illustrated fixation lamp display changing unit can change the size of display of the fixation lamp 106. For example, if the fixation lamp 106 is a liquid crystal display (LCD) and can display a two-dimensional image, the size of the displayed two-dimensional image may be changed in the X and Y directions. If the fixation lamp 106 is a point light source, an optical member such as a lens may be added so that the size of the point light source can be changed. The fixation lamp 106 can be magnified or reduced by moving the position of the optical member with respect to the subject's eye 100. Alternatively, the optical path L2 may include X and Y scanners. The point light source is turned on and off to generate a two-dimensional image by using the X and Y scanners. In such a case, the point light source may be turned on and off at different timing so that the X and Y scanners can generate two-dimensional images of different sizes.

The fixation lamp 106 capable of changing a display size is used to change the size of the fixation lamp 106 in the following manner. Initially, the operator specifies an imaging range. If the OCT apparatus increases the imaging distance P0 according to the imaging range, the optical path length of the measurement light increases. The fixation lamp 106 moves away from the subject's eye 100 and appears smaller. In such a case, the OCT apparatus can make the display of the fixation lamp 106 larger so that the size of the fixation lamp 106 with respect to the subject's eye 100 remains constant. If the OCT apparatus reduces the imaging distance P0, the optical path length of the measurement light decreases. The fixation lamp 106 approaches the subject's eye 100 and appears larger. In such a case, the OCT apparatus displays the fixation lamp 106 smaller. In other words, the OCT apparatus changes the size of the fixation lamp 106 in an interlocking manner with the imaging distance P0 to make the apparent size of the fixation lamp 106 constant.

The present invention is not limited to the foregoing exemplary embodiments, and various changes and modifications may be made without departing from the gist of the foregoing exemplary embodiments. For example, while the foregoing exemplary embodiments have dealt with the case where the object to be measured is the eye, the exemplary embodiments may be applied to objects to be measured other than the eye. Examples include the skin and organs. In such cases, the exemplary embodiments of the present invention are configured as medical apparatuses other than an ophthalmologic apparatus, such as an endoscope. The subject's eye described above can thus be regarded as an object.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-017658 filed Jan. 31, 2013, which is hereby incorporated by reference herein in its entirety.

What is claimed is:

1. An optical tomographic imaging apparatus configured to obtain a tomographic image of an anterior eye based on light into which return light from the anterior eye irradiated with measurement light and reference light corresponding to the measurement light are combined, the optical tomographic imaging apparatus comprising:
a measurement light optical path length changing unit configured to change an optical path length of the measurement light;
an instruction unit configured to input an instruction on a size of an imaging range of the tomographic image;
a detecting unit configured to detect, based on an output of an imaging unit which is configured to image the anterior eye, a position gap between the anterior eye and an optical unit including an optical path of the measurement light in a depth direction of the anterior eye after the instruction; and
a control unit configured to control the measurement light optical path length changing unit to change the optical path length of the measurement light by the detected position gap and a distance corresponding to a change of the size.

2. The optical tomographic imaging apparatus according to claim 1,
wherein the measurement light optical path length changing unit includes an optical unit moving mechanism configured to move the optical unit with respect to the anterior eye, and
wherein the control unit is configured to control the optical unit moving mechanism to change the optical path length of the measurement light by the detected position gap and the distance corresponding to the change of the size.

3. The optical tomographic imaging apparatus according to claim 1, further comprising:
a display control unit configured to cause a display unit to display a display pattern for inputting an instruction on a change of the size of the imaging range of the tomographic image,
wherein the instruction unit is configured to input an instruction on the change according to an operation by an operation unit.

4. The optical tomographic imaging apparatus according to claim 1, further comprising:
a reference light optical path length changing unit configured to change an optical path length of the reference light,
wherein the control unit is configured to control the measurement light optical path length changing unit and the reference light optical path length changing unit in an interlocking manner according to the instruction.

5. The optical tomographic imaging apparatus according to claim 1, further comprising:

a moving unit configured to move a focusing lens along an optical path, the focusing lens focusing the measurement light on the anterior eye, wherein the control unit is configured to control the measurement light optical path length changing unit and the moving unit in an interlocking manner according to the instruction.

6. The optical tomographic imaging apparatus according to claim 1, further comprising:

a fixation lamp display changing unit configured to change a display size of a fixation lamp, wherein the control unit is configured to control the fixation lamp display changing unit in association with the measurement light optical path length changing unit according to the instruction.

7. An optical tomographic imaging apparatus configured to obtain a tomographic image of an anterior eye based on light into which return light from the anterior eye irradiated with measurement light and reference light corresponding to the measurement light are combined, the optical tomographic imaging apparatus comprising:

a measurement light optical path length changing unit configured to change an optical path length of the measurement light;

a fixation lamp display changing unit configured to change a display size of a fixation lamp;

an instruction unit configured to input an instruction on a size of an imaging range of the tomographic image; and a control unit configured to control the fixation lamp display changing unit in association with the measurement light optical path length changing unit according to the instruction.

8. The optical tomographic imaging apparatus according to claim 6, wherein the control unit is configured to, in a case where an instruction to increase the imaging range is input, control the fixation lamp display changing unit in association with the measurement light optical path length changing unit to increase the optical path length of the measurement light and increase the display size of the fixation lamp.

9. The optical tomographic imaging apparatus according to claim 1, further comprising a storage unit configured to store at least one of a table and an expression indicating a relationship between the size of the imaging range of the tomographic image and the optical path length of the measurement light, wherein the control unit is configured to control the measurement light optical path length changing unit by using the at least one stored in the storage unit according to the instruction by the instruction unit.

10. The optical tomographic imaging apparatus according to claim 1, further comprising a scanning unit configured to scan the anterior eye with the measurement light and be rotatable in one direction.

11. The optical tomographic imaging apparatus according to claim 1, further comprising a scanning unit configured to scan the anterior eye with the measurement light, wherein the control unit is configured to control the scanning unit so as not to change of the optical path length of the measurement light reaches a limit, change a scan angle of the scanning unit.

12. A method for controlling an optical tomographic imaging apparatus configured to obtain a tomographic image of an anterior eye based on light into which return light from the anterior eye irradiated with measurement light and reference light corresponding to the measurement light are combined, the method comprising:

inputting an instruction on a size of an imaging range of the tomographic image;

detecting, based on an output of an imaging unit which is configured to image the anterior eye, a position gap between the anterior eye and an optical unit including an optical path of the measurement light in a depth direction of the anterior eye after the instruction; and controlling a measurement light optical path length changing unit to change an optical path length of the measurement light by the detected position gap and a distance corresponding to a change of the size, the measurement light optical path length changing unit being configured to change the optical path length of the measurement light.

13. The method according to claim 12, further comprising controlling a fixation lamp display control unit in association with the measurement light optical path length changing unit according to the instruction, the fixation lamp display changing unit being configured to change a display size of a fixation lamp.

14. A method for controlling an optical tomographic imaging apparatus configured to obtain a tomographic image of an anterior eye based on light into which return light from the anterior eye irradiated with measurement light and reference light corresponding to the measurement light are combined, the method comprising:

inputting an instruction on a size of an imaging range of the tomographic image; and controlling a fixation lamp display changing unit in association with the measurement light optical path length changing unit according to the instruction, the measurement light optical path length changing unit being configured to change an optical path length of the measurement light, the fixation lamp display changing unit being configured to change a display size of a fixation lamp.

15. The method according to claim 13, further comprising:

controlling, in a case where an instruction to increase the imaging range is input, the fixation lamp display control unit in association with the measurement light optical path length changing unit to increase the optical path length of the measurement light and increase the display size of the fixation lamp.

16. A non-transitory computer-readable storage medium storing a program that causes a computer to perform the method according to claim 12.

17. A non-transitory computer-readable storage medium storing a program that causes a computer to perform the method according to claim 14.

18. The method according to claim 12, further comprising:

scanning, by a scanning unit, the anterior eye with the measurement light, wherein the scanning unit is controlled so as not to change a scan angle of the scanning unit.

* * * * *